United States Patent [19]

Bergman et al.

[11] 4,241,216

[45] Dec. 23, 1980

[54] PHTHALIC ACID DIESTER PREPARATION WITH WASTE STREAM PURIFICATION AND RECYCLE

[75] Inventors: Lee H. Bergman, Baton Rouge, La.; John J. Evangelista, New Boston, Mich.; William M. Herring, Hackettstown, N.J.

[73] Assignee: BASF Wyandotte Corporation, Wyandotte, Mich.

[21] Appl. No.: 6

[22] Filed: Jan. 2, 1979

[51] Int. Cl.$^3$ .............................................. C07C 67/08
[52] U.S. Cl. ...................................... 560/99; 560/98; 560/78; 560/191; 560/203
[58] Field of Search ...................... 560/191, 98, 78, 99

[56] References Cited

U.S. PATENT DOCUMENTS

| | | | |
|---|---|---|---|
| 3,547,283 | 12/1970 | List et al. | 560/98 |
| 3,705,186 | 12/1972 | Naskar et al. | 560/78 |
| 3,843,697 | 10/1974 | Khaidukor et al. | 560/191 |
| 3,886,199 | 5/1975 | Suter et al. | 560/98 |
| 3,896,159 | 7/1975 | Kratzer et al. | 560/191 |
| 4,066,835 | 1/1978 | Hahn et al. | 560/98 |

*Primary Examiner*—James H. Reamer
*Attorney, Agent, or Firm*—Andrew E. Pierce

[57] ABSTRACT

A continuous process for the preparation in at least one esterification reactor of phthalate diesters utilizing phthalic acid or anhydride and a stoichiometric excess of at least one saturated aliphatic alcohol containing about 4 to about 10 carbon atoms comprises (a) reaction of phthalic acid or anhydride with said alcohol in a reactor zone, (b) purification of the diester in a purification zone in which the reaction product is neutralized with an alkali metal hydroxide, i.e., sodium hydroxide, to separate the diester and the unreacted phthalic acid or anhydride together with said saturated alcohol utilized in the reaction, said reaction product is separated into an organic phase and an aqueous waste phase. The organic phase is washed with water, steam stripped, treated with activated charcoal and filtered to purify the diester product desired, (c) the aqueous phase containing monoester is separated from said organic phase in step (b) is purified by filtration to remove solid impurities, carbon treated to remove color bodies, and acidified and extracted with the same alcohol used in the esterification to obtain an organic phase which can be recycled to the reaction zone of the process without causing discoloration of the desired diester product of the process.

In the monoester purification process, acidification is accomplished utilizing a strong organic acid, i.e., sulfuric acid, prior thereto or simultaneously with extraction utilizing the same alcohol used in the esterification process. Purification of the aqueous waste streams produced in the process can be accomplished using activated charcoal to remove organic wastes and precipitation of inorganic salts to remove inorganic impurities produced in the process.

16 Claims, 3 Drawing Figures

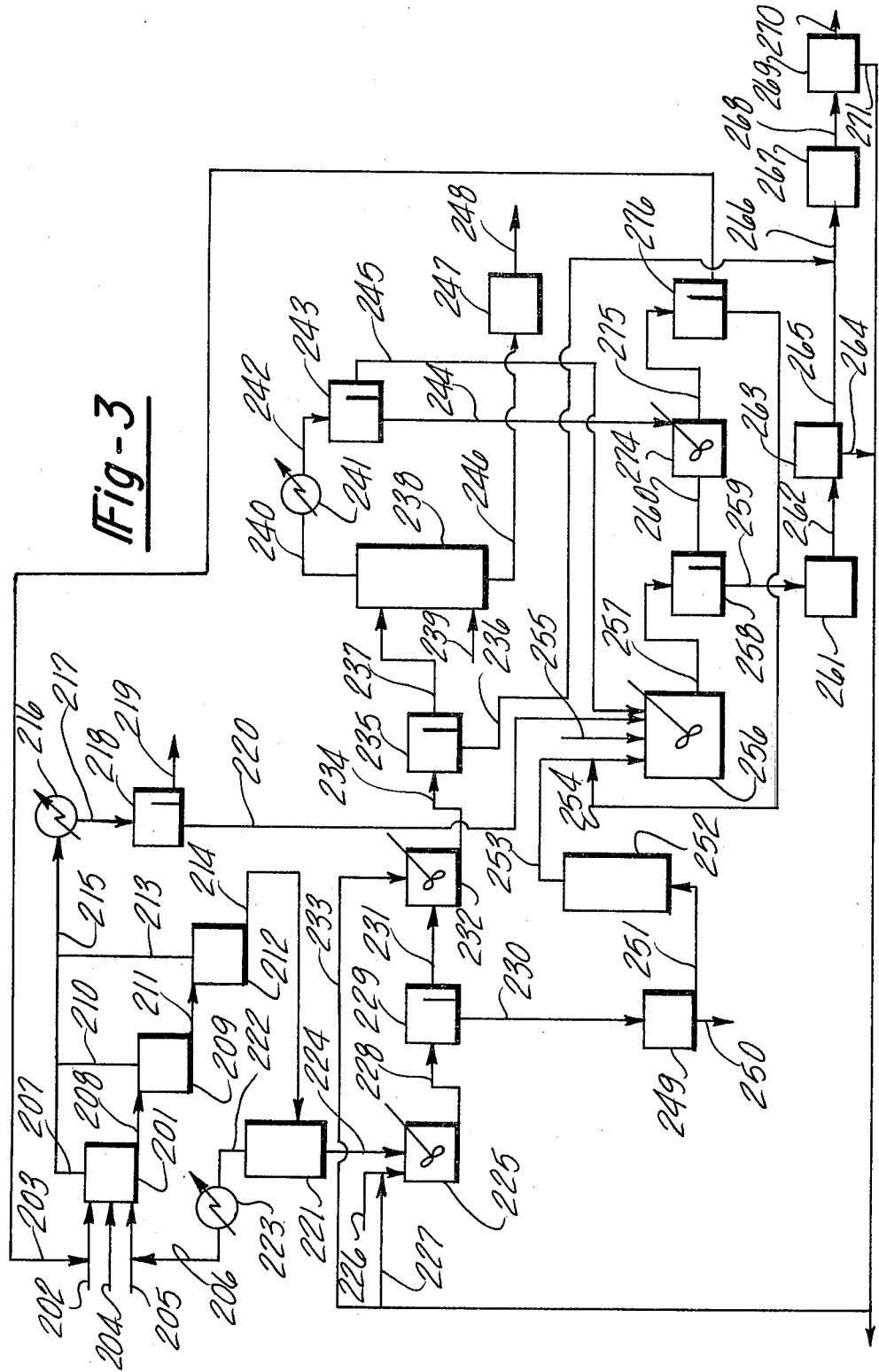

Page 1

PHTHALIC ACID DIESTER PREPARATION WITH WASTE STREAM PURIFICATION AND RECYCLE

BACKGROUND OF THE INVENTION

1. Field of the Invention

This invention relates to a continuous process for the preparation of phthalic esters of saturated alcohols wherein the waste streams obtained in the process are purified so as to permit recycling of organic by-products and unreacted components to the process.

2. Description of the Prior Art

Continuous processes for the production of phthalic esters from saturated alcohols are known in the prior art. Recycling of the monoester by-product obtained by extraction of the product of the esterification utilizing the same alcohol used for the esterification is disclosed by Suter et al in U.S. Pat. No. 3,886,199. However, it has been found that, where the monoester is recycled, discoloration of the desired diester product occurs, especially where process conversion to the diester is about 90 to about 98 percent. In U.S. Pat. No. 3,896,159, Kratzer et al, there is disclosed an improvement in the process of preparing phthalic esters from saturated alcohols wherein a substantial reduction in the waste water discharged from the process is obtained by the utilization in the process of water generated in the esterification reaction thus reducing the amount of waste water by about 75 percent of the original amount produced in a conventional process. Helgorsky et al in U.S. Pat. No. 3,933,630 disclose a critical free-acidity is necessary for the desired purification of an acidified water phase obtained subsequent to neutralization of the reaction product of the esterification in a process for the production of phthalic esters. This permits the acidified water phase to be subsequently extracted with the same alcohol used in the esterification process and, without further purification, recycled to the esterification process.

Recently, in U.S. Pat. No. 4,066,835 to Hahn et al, there is disclosed a process for the purification of waste water produced in the process of producing diester plasticizer such as dioctyl phthalate wherein organic components in the waste water produced in the process are removed and subsequently recycled to the esterification process by heating the aqueous phase obtained subsequent to separation of the diester reaction product. The process consists of heat treating said aqueous phase to a temperature of above 200° C. under the appropriate pressure to form an organic phase and an aqueous phase, the organic phase is then removed and recycled to the process. The recycled organic phase does not disadvantageously affect the production of the ester or detract from the quality of the ester produced. The remaining aqueous phase is then readily purified so as to meet environmental standards.

In no one of the references cited, is a process disclosed for the production of phthalic esters wherein both organic and inorganic impurities are removed from the desired reaction product utilizing conventional process steps and recycled to the process. The recycle to the process of all organic waste products and all waste water produced in the process is not disclosed in the prior art.

SUMMARY OF THE INVENTION

Broadly, this invention relates to continuous processes for removing organic waste components from all process streams as well as the waste water effluent obtained in the production of a diester plasticizer produced by esterification of phthalic acid or anhydride with a saturated aliphatic alcohol containing about 4 to about 10 carbon atoms either in the presence or absence of esterification catalysts wherein said waste water effluent contains an organic by-product of said process, namely the monoester reaction product in addition to unreacted phthalic acid or anhydride and said saturated aliphatic alcohols. The process comprises continuously feeding phthalic acid or anhydride together with said alcohol to a reaction zone while continuously removing water of esterification formed in the reaction together with a portion of said alcohol, discarding or recycling to the process said water of esterification and recycling said alcohol to the process. An esterification temperature of about 100° C. to about 250° C. is used in the reaction zone to obtain a conversion of said acid or anhydride of at least 90 percent whereupon the reaction mixture is mixed with an aqueous alkali to solubilize therein the monoester by-product and the mixture is allowed to separate into two phases, the first aqueous phase and the first organic phase and thereafter said organic phase is washed with water and subsequently decolorized by steam distillation, treated with activated charcoal and filtered to yield the desired diester product. The monoester reaction product is recycled to the reaction zone after treatment of said first aqueous phase by filtration and with activated carbon to remove solids and color bodies. Subsequently, said first aqueous phase waste water is acidified with a strong acid, such as sulfuric acid, to obtain a free-acidity of said phase which is greater than 0.03 Normal. Thereafter, said first aqueous phase is mixed with about 5 to about 25 percent by weight of the same saturated aliphatic alcohol used in the esterification, said weight based upon the weight of said first aqueous phase, and the resulting mixture is separated into a second organic phase and a second aqueous phase which is discarded or recycled to the process. Said second organic phase is mixed with about 50 to about 200 percent by weight of water based upon the weight of said second organic phase and the resulting mixture is separated into a third organic phase and a third aqueous phase. Said third organic phase is recycled to the esterification reaction zone and said third aqueous phase is discarded or recycled to the process.

In an alternative process, all process waste water is either used in the process or passed through activated charcoal prior to discarding in order to reduce the biological oxygen demand or chemical oxygen demand of the water. In another alternative process, all liquid waste water streams are recycled to the process, excess water being removed as required, by purging the system, the water being suitable for on site process use. Desirably, the water from a steam-stripping stage is used to wash the monoester by-product to remove traces of sodium used in neutralization.

Prior to recycling the stream containing said monoester to the process, solids are removed by filtration and color bodies are removed by carbon treatment from said first aqueous phase and the monoester by-product is then rendered insoluble by acidification. An organic phase is obtained thereafter by decantation which is then washed in a washing stage. The waste water effluent from the steam stripping stage which is composed of water and organic impurities is used in this washing stage. Subsequent to washing, a second organic phase obtained by decantation subsequent to acidification, is washed and again decanted and a third organic phase obtained is recycled to the reaction. The third aqueous phase obtained is discarded or led to the acidification zone in the process.

The waste water from the monoester acidification decanter can be combined with the waste water from the diester wash decanter and treated with activated carbon to remove organic impurities. Further treatment by evaporation can effect the removal of inorganic salts to allow recycling, after condensation, of this liquid waste back to the process. The ever increasing volumes of water resulting from the water of esterification and the steam used in stripping are removed occasionally by a purge of the system. This water is suitable for use in the process or in other on site processes.

DESCRIPTION OF THE DRAWINGS

The features and advantages of the present invention will become apparent from the following description thereof which is to be read with reference to the accompanying drawings wherein:

FIGS. 1, 2, and 3 are schematic representations of useful procedural sequences for producing diesters of phthalic acid continuously in accordance with the invention.

Referring to FIG. 1, phthalic anhydride and a desired alcohol containing about 4 to about 10 carbon atoms, such as 2-ethyl hexyl alcohol, are continuously fed respectively through pipes 2 and 5 to a reactor 1 in a reaction zone containing a plurality of reactors, shown as 1, 9, and 12, preferably arranged as shown so that successive reactors 9 and 12 are gravity fed through pipes 8 and 11 from the preceding reactor. Where appropriate, catalyst is fed through pipe 4. Alternatively, feed to successive reactors 9 and 12 can be accomplished by pumps, not shown in FIG. 1. Recycle monoester is fed through pipe 3 to reactor 1. Water of esterification is removed as vapor through pipes 7, 10, and 13 and the combined vapor in pipe 15 is condensed in heat exchanger 16 and then led through pipe 17 to decanter 18. The organic layer is removed through pipe 19 and incinerated and the aqueous layer is led to the acidification zone, 56. Excess water of reaction is returned to the process through pipe 20.

Figure 1:
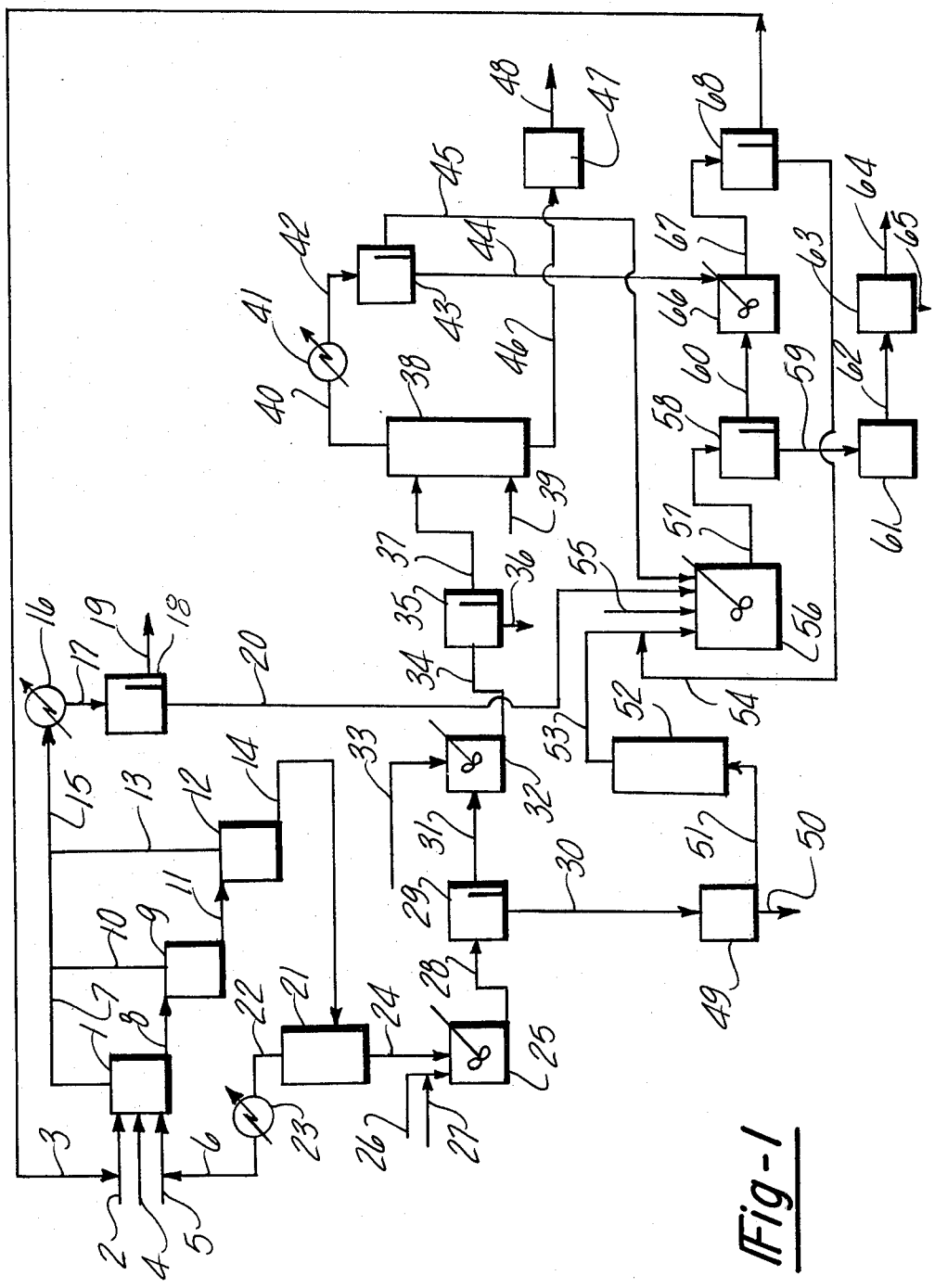

The reaction product of the reaction zone (reactors 1, 9, and 12) leaves reactor 12 through pipe 14 and is flashed in evaporator 21 where most of the excess alcohol is removed through pipe 22, condensed in heat exchanger 23 and recycled to the process through pipe 6. The stripped diester is led through pipe 24 to the neutralization stage 25 of the diester purification zone (stages 25, 29, 32, 35, 38, and 47) where said product enters stage 25 through pipe 24 and is mixed with an aqueous solution of a base such as an alkali metal hydroxide, i.e., sodium hydroxide which enters through pipe 26. Additional water enters through pipe 27. The neutralized reaction product is led through pipe 28 to decanter stage 29 where a first organic phase is separated and led through pipe 31 to washing stage 32. Water is added through pipe 33 to said washing stage. The first aqueous phase leaves through pipe 30 for further use in the process. Said first organic phase is washed clean of sodium hydroxide residues, passes through pipe 34 to decanter stage 35 and discharged through pipe 36. The purified organic phase is led through pipe 37 to steam stripping stage 38 for further purification to remove the remaining alcohol in the first organic phase. Steam enters stage 38 through pipe 39.

Said impurities are removed with steam through pipe 40, condensed in stage 41 and led through pipe 42 to decanter 43. The alcohol layer is removed through pipe 45 and is led to the acidification stage 56 and the water layer is removed through pipe 44 and led to washing stage 66 where it is utilized for washing the recovered monoester. The purified first organic phase passes through pipe 46 to treatment stage 47 wherein activated carbon treatment and filtration is used to remove the remaining impurities and the purified diester leaves through pipe 48.

The first aqueous phase separated in decanter stage 29 is led through pipe 30 and enters filtration stage 49 of the monoester purification zone (stages 49, 52, 56, 58, 66, and 68) wherein solid waste is removed through pipe 50 and the filtered aqueous phase is led through pipe 51 to carbon treating and filtration stage 52 wherein color bodies are removed, the purified aqueous phase is led through pipe 53 and enters acidification stage 56. A strong mineral acid solution, i.e., sulfuric acid solution, enters through pipe 55, the condensed alcohol from stage 43 enters through pipe 45. Water of reaction enters through pipe 20. After extraction with the alcohol, the acidified aqueous phase, having a free acidity greater than 0.03 Normal, is led thorough line 57 to decanter stage 58 wherein a second aqueous phase is discharged through line 59 and an organic phase is separated and led through line 60 to washing and mixing stage 66 which is fed through pipe 44 with the aqueous phase from the decanter 43. The washed second organic phase is led through line 67 to decanter stage 68 wherein a third organic phase is separated which leaves through line 3 for recycle to reactor stage 1 of the reaction zone. The third aqueous phase is discharged through line 54 and recycled to acidification stage 56. The second aqueous phase, obtained through pipe 59, is cooled in stage 61 and led through pipe 62 to filter 63 where insolubles are removed through pipe 65 and aqueous waste discharged through pipe 64.

Figure 2:
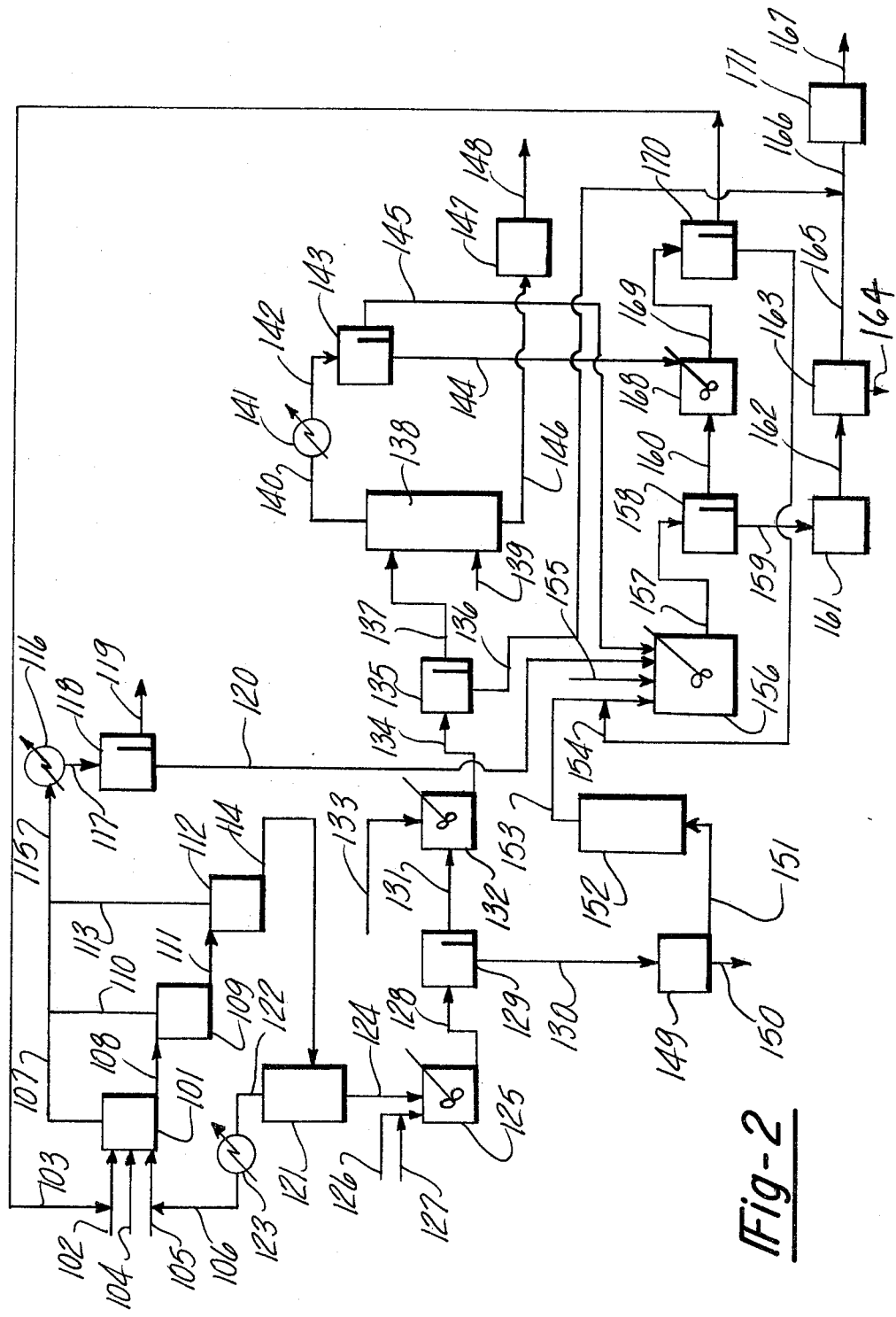

Referring now to FIG. 2 which is a schematic representation of an alternative useful procedural sequence for producing diesters of phthalic acid continuously in accordance with the present invention, a desired alcohol containing about 4 to about 10 carbon atoms, i.e., 2-ethyl hexyl alcohol, is continuously fed through pipe 105 and phthalic acid or phthalic anhydride is fed through pipe 102 to reactor stage 101 in a reaction zone (stages 101, 109, and 112) having a plurality of reactor stages. In addition, recycle monoester is fed to reaction stage 101 through line 103 and where appropriate, catalyst is fed through pipe 104. Reaction stages 101, 109 and 112 are connected respectively as shown by pipe 108 and pipe 111. Water of reaction together with volatile organic by-products leave through pipes 107, 110 and 113 and are conducted through pipe 115 to condenser stage 116. The condensate leaves through pipe 117 and enters decanter stage 118 from which an organic layer is discharged through pipe 119 for disposal by incineration. The aqueous waste from said decanter stage is led through pipe 120 to the acidification stage 156. The product of the reaction zone is led through pipe 114 to flash stripper stage 121 from which alcohol vapor, which exits through pipe 122, is condensed in stage 123 and recycled to the esterification zone through pipe 106.

The stripped product is led through pipe 124 to the neutralization stage 125 of the diester purification zone (stages 125, 129, 132, 135, 138, and 147) where it is mixed with an aqueous solution of a base, such as an alkali metal hydroxide, i.e., sodium hydroxide which enters stage 125 through pipe 126 and water which enters through pipe 127. The product of the reaction zone contains unreacted phthalic acid and said alcohol together with the monoester by-product which upon neutralization is rendered water soluble. The mixture is led through pipe 128 to decanter stage 129 wherein a first organic phase is separated and led through pipe 131 to washing stage 132 and a first aqueous phase is led through pipe 130 for further treatment in the process. In washing stage 132, the first organic phase is washed with water which enters through pipe 133, the organic phase passing together with water through line 134 to decanter stage 135 and then to steam stripping stage 138 through pipe 137. Steam enters stage 138 through pipe 139. Waste water from said decanter is passed through pipe 136 for further use in the process. In said steam stripping stage, the volatile components of the first organic phase, together with the steam used for stripping, leave through line 140 and pass to condenser stage 141 where condensation takes place. Condensate is discharged through pipe 142 and passes to decanter stage 143. The alcohol layer from this stage is led through pipe 145 to the acidification stage 156, the water layer leaving through pipe 144. The purified first organic phase passes through pipe 146 to treatment stage 147 wherein impurities are separated by treatment with activated carbon and removed by filtration. Pure diester is obtained through pipe 148.

The first aqueous phase leaving decanter stage 129 passes through pipe 130 and enters the filtration stage 149 of the monoester purification zone (stages 149, 152, 156, 158, 168, and 170) wherein solid particles are removed through pipe 150 and the filtered first aqueous phase passes through pipe 151 to carbon treating and filtration stage 152. The purified first aqueous phase leaves through pipe 153 and enters acidification stage 156. A strong mineral acid solution, i.e., sulfuric acid, is added through pipe 155 and waste alcohol from steam stripping stage 138 enters through pipe 145. By-product waste water from the reaction zone decanter 118 enters the acidification stage 156 through pipe 120. In said acidification stage, a free acidity is attained of greater than 0.03 Normal. After extraction with said alcohol, said first aqueous phase then passes through pipe 157 to decanter stage 158 wherein a second organic phase is separated and passes through pipe 160 to washing stage 168. In said washing stage, the water layer from decanter stage 143 enters through pipe 144 and is mixed with the second organic phase, the mixture leaving through pipe 169 and passing to decanter stage 170 wherein a third organic phase is separated which leaves through pipe 103 for recycle to reactor 101 in the reaction zone and a third aqueous phase leaves through line 154 for recycle to the acidification stage. The second aqueous phase leaves decanter stage 158 through pipe 159, is cooled in stage 161, passes through pipe 162 to filtration stage 163 and insolubles are removed through pipe 164. The filtrate is passed to activated carbon treating and filtration stage 171 through pipes 165 and 166 after being joined by aqueous waste water leaving the diester wash decanter through pipe 136. Purified waste water is recycled to the process or discharged through line 167.

Referring now to FIG. 3 which is a schematic representation of an alternative useful procedural sequence for producing diesters of phthalic acid continuously according to the present invention, a desired alcohol containing about 4 to about 10 carbon atoms is fed continuously through pipe 205 to esterification stage 210 in an esterification zone containing a plurality of esterification stages (201, 209, and 212). Where appropriate, catalyst is fed through pipe 204. Phthalic acid or phthalic anhydride is fed through pipe 202 to said stage and recycled monoester is fed through pipe 203 to said esterification stage. Esterification stages 201, 209, and 212 are connected as shown by pipes 208 and 211 and water of reaction leaves these reaction stages respectively through pipes 207, 210, and 213. The water of reaction is led through pipe 215 to condenser stage 216 entering decanter stage 218 through pipe 217. An organic layer is removed through pipe 219 for subsequent incineration and the aqueous layer leaves through pipe 220 and enters acidification stage 256.

The product obtained in the reaction zone leaves reaction stage 212 through pipe 214 and enters flash stripper stage 221 from which alcohol is removed as vapor through pipe 222 which is then condensed in condenser stage 223 and recycled through pipe 206 to the reaction zone. The stripped diester enters neutralization stage 225 of the diester purification zone (stages 225, 229, 232, 235, 238, and 247) through pipe 224 for mixture with an aqueous solution of a base such as an alkali metal hydroxide, i.e., sodium hydroxide, which is added to said neutralization stage through pipe 226. Recycle waste water is led through pipe 227 to said neutralization stage. After neutralization, the mixture is led through pipe 228 to decanter stage 229 wherein a first organic phase is separated and is passed through pipe 231 to washing stage 232. A first aqueous phase leaves stage 229 through line 230 for further treatment in the process. In washing stage 232, said first organic phase is washed to remove residual sodium hydroxide using waste water which enters through pipe 233 and is led through pipe 234 to decanter stage 235, waste water is removed as aqueous phase through pipe 236 for recycle to the process and the organic phase is led through pipe 237 to steam stripping stage 238, the waste water leaving through pipe 236 for further use in the process. In said steam stripping stage steam enters through pipe 239 and said first organic phase is purified of volatiles including unreacted alcohol and water and the purified diester is passed through pipe 246 to treatment stage 247 wherein impurities are separated by activated carbon treatment and removed by filtration. The purified diester leaves through pipe 248. Volatiles are removed through pipe 240 and pass to condenser stage 241. Condensate is led through pipe 242 to decanter stage 243. The organic phase leaves through pipe 245 and the aqueous phase passes through pipe 244 to washing stage 247.

Said first aqueous phase after leaving decanter stage 229 through pipe 230 is led to filtration stage 249 of the monoester purification zone (stages 249, 252, 256, 258, 274 and 276). Solid waste is discharged through pipe 250, the purified first aqueous phase being passed through pipe 251 to a carbon treating and filtration stage 252 wherein color bodies are separated from the purified first aqueous phase which leaves through pipe 253 and passes to an acidification stage 256. In stage 256, an aqueous solution of a strong mineral acid such as sulfuric acid enters through pipe 255, alcohol from decanter stage 243 enters through line 245, waste water from the reactor zone decanter stage 218 enters through pipe 220 and recycle wash water enters through pipe 254, a free acidity being obtained in said acidification stage of greater than 0.03 Normal. The acidified first aqueous phase after alcohol extraction is then passed through pipe 257 to decanter stage 258 wherein a second organic phase is separated and is passed through pipe 260 to a washing stage 274. In washing and mixing stage 274, said second organic phase is washed with the aqueous layer from said decanter, stage 243, the mixture leaving through pipe 275 and entering decanter stage 276 wherein a third organic phase is separated which leaves through pipe 203 for recycling to reaction stage 201. A third aqueous phase separated in stage 276 leaves through pipe 254 for recycling to the acidification stage 256.

The waste water leaves decanter stage 258 through pipe 259, is cooled in stage 261 and passed through pipe 262 to filtration stage 263 wherein insolubles are removed through pipe 264. The filtrate is led through pipe 265 and mixed with the waste water from decanter stage 235 and passed through pipe 266 to carbon treatment and filtration stage 267. The purified waste water passes through line 268 to evaporator stage 269 wherein inorganic salts are separated and removed through pipe 270. The aqueous vapors are discharged or condensed and passed through pipe 271 for recycle to the process passing through pipe 227 to neutralization stage 225 and through pipe 233 to washing stage 232. Excess water is purged from the system for use in other on site processes.

Means for heating the reactor stages in the reaction zone can be by the use of hot oil. Means for regulating the amount of steam are not shown in FIGS. 1, 2 and 3 but any conventional means known in the art can be utilized.

The reaction product from the first stage reactor in the reaction zone is led to successive stage reactors by gravity as shown in FIGS. 1, 2 and 3 but can be sent to successive reactors by a pump, if the reactors are placed on the same level. The reaction is thus carried out in a similar manner in successive reactors in either of these arrangements. Where the reaction is catalyzed, generally catalyst is supplied only to the first of the reactors arranged in successive stages.

DETAILED DESCRIPTION OF THE INVENTION

Generally the process of the present invention is carried out by reacting a saturated aliphatic alcohol containing about 4 to about 10 carbon atoms with phthalic acid or anhydride to obtain the desired diester reaction product.

While the process is particularly concerned with the production of the highly advantageous diesters of phthalic acid which are required in large quantities for use as plasticizers for organic polymers such as polyvinyl chloride, the process of the invention is also applicable to the production of esters of suitable aliphatic and other aromatic dicarboxylic acids or anhydrides thereof, for example, maleic anhydride, fumaric acid, and other dicarboxylic acids of the formula

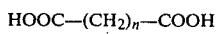

HOOC—(CH$_2$)$_n$—COOH in which n denotes a whole number of from 1 to 8, as exemplified by such acids as malonic acid, succinic acid, glutaric acid, adipic acid, pimelic acid, suberic acid, azelaic acid, and sebacic acid. Examples of suitable saturated aliphatic alcohols having about 4 to about 10 carbon atoms are butanol, n-octanol-1, n-octanol-2, 2-ethyl-hexanol-1, n-nonyl alcohol, isodecanol, and decanol.

The process can take place in the presence of a catalyst or without catalyst. The catalysts are generally strong mineral acids such as sulfuric acid or hydrochloric acid, and aromatic sulfonic acids, such as benzene sulfonic acid, para toluene sulfonic acid, and mixtures thereof. In addition, aluminum chloride, zinc chloride, and Lewis acids such as boron trifluoride are also useful catalysts as are aliphatic sulfonic acids. In addition, amphoteric-based compounds have been used as catalysts, for example, divalent tin oxide, divalent tin oxylate, metallic tin, bismuth oxide and mixtures thereof. These amphoteric-based catalysts have been, however, mostly used in batch processes for the production of phthalic esters.

Recently, lower alkyl titanium esters and lower alkyl zirconium esters have been utilized as catalysts for the production of phthalic esters in both batch and continuous processes. Generally said ester catalysts contain about 3 to about 8 carbon atoms in the alkyl group. Useful examples of the titanium esters are isopropyl titanate, 2-ethyl hexyl titanate and n-butyl titanate.

The use of an autocatalytic system for the production of phthalic esters also has been widely used in order to produce a phthalic ester product free of catalytic impurities. Such processes require use of higher temperatures, however, to obtain appropriate yields and a suitable rate of reaction. For instance, in an autocatalytic process for production of phthalic esters in the absence of esterification catalyst, it is common to conduct the reaction at a temperature of about 150° C. to 250° C. It will be noted that the temperature of reaction will also vary according to the particular starting alcohols used, the reaction being conducted at the boiling point of the alcohol-ester mixture, and also to some extent upon the stability of the diesters produced in the process. Thus, if the temperature is excessive, discoloration of the product or an extensive loss of starting alcohol occurs. Utilizing an acid catalyst such as a strong mineral acid, as has been described, it is possible to reduce the reaction temperature range to about 100° C. to about 200° C. This temperature range for the reaction also applies to reactions catalyzed with titanium or zirconium alkyl esters.

The amount of catalyst utilized is about 0.1 percent to about 3 percent by weight of the reactants where the esterification catalyst is, for example, a strong mineral acid, a Lewis acid, a sulfonic acid, or an amphoteric-based compound. Where the catalyst is a titanium or zirconium ester, the amount used is generally about 0.04 percent to about 0.2 percent.

The esterification of the starting acid or anhydride and alcohol is generally carried out in the usual manner in the absence of entraining agents or carriers and preferably by continuously charging the mixture of the desired saturated aliphatic alcohol containing about 4 to about 10 carbon atoms, phthalic acid or anhydride with or without appropriate catalyst to a single reactor or the first of a plurality of reactors arranged preferably in order from a higher position to a lower position, the reaction being effected at the boiling temperature of the mixture, preferably with stirring while distillation of the water of esterification and/or alcohol-water azeotrope is continuously maintained.

In the production of the esters in accordance with the invention, the esterification alcohol is used in an amount in excess of the stoichiometric amount to produce the diester, generally a stoichiometric excess of about 10 to about 50 percent by weight is used, preferably about 10 to about 30 percent by weight excess alcohol is used all based upon the weight of said starting acid or anhydride. The excess alcohol is condensed in heat exchanger stage 16, 116, or 216 and recycled to the process. The alcohol thus separated from the desired diester reaction product is then utilized to extract the monoester reaction by-product subsequent to or simultaneously with the acidification of the first aqueous phase which is removed from the reaction product subsequent to neutralization thereof. The amount of alcohol used to extract said monoester from said aqueous phase is generally about 5 percent to about 25 percent by weight, preferably about 5 to about 15 percent by weight, and most preferably about 5 to about 10 percent by weight, all based on the weight of said first aqueous phase.

Generally the process of the invention is conducted in the absence of entrainers or carriers such as the inert organic solvents described in U.S. Pat. No. 3,476,796. Such inert organic solvents which have low solubility in water and are capable of forming azeotropic compositions with water have been found unnecessary in the process of the invention to obtain the high yields and purity of reaction product as well as purification of waste streams produced in the process.

In accordance with the process of the invention, as illustrated by FIG. 1, the incidence of waste water is the same as that produced in the process of the prior art for the production of dioctyl phthalate. In the process illustrated by the schematic representation of FIG. 1, the only waste waters discharged in the process are the streams produced upon decanting the second organic phase in decanter stage 68 and that produced on decanting after washing the first organic phase in decanter stage 35. These waste water streams contain mainly inorganic salts produced by the neutralization of the residual alkali metal hydroxide with the strong mineral acids utilized to acidify the first aqueous phase. As such, these waste streams are not presently objectionable from an ecological standpoint since they do not have a high biological oxygen demand or a high chemical oxygen demand.

With respect to the processes illustrated by FIGS. 2 and 3, all waste water streams in the respective processes are either passed through activated charcoal to purify these streams prior to discharge to the environment or, alternatively, passed to an evaporation stage wherein inorganic salts are removed as solids and the aqueous vapors, after condensation, recycled to the process thus avoiding discharge of waste water to the environment.

The esterification process of the invention is conducted at a level of acid to ester conversion of at least 90 percent and preferably 92 to 99 percent. In the presence of a catalyst, the esterification reaction proceeds at such a rate that a conversion of about 98 to about 99 percent is achieved.

In the neutralization stage of the reaction, as is conventional, only sufficient aqueous alkali metal hydroxide, for instance, sodium hydroxide or an alkali metal carbonate, for instance, sodium carbonate, in solution is used to neutralize the reaction product. In the neutralization stage which is conducted at a temperature of about 80° C. to about 100° C., there are formed alkali metal salts of the organic acid utilized in the reaction, particularly the monoester salt. The salts also can include those of the strong mineral acids utilized as catalyst in the reaction. All these salts are water soluble and are thus separated from the desired diester product which has very low solubility in water. By contrast, in the subsequent acidification of the first aqueous phase containing said soluble esters, it has been found desirable to acidify said aqueous phase with an excess of a strong acid so as to insure complete insolubilization of the monoester by-product in addition to the other esters described above. Thus, utilizing a strong acid such as sulfuric acid, a free acidity of the waste water of greater than 0.03 Normal, preferably 0.03 to 0.1 Normal, and most preferably about 0.03 to about 0.05 has been found desirable, the acidification being conducted simultaneously or prior to extraction of said first aqueous phase utilizing the same alcohol used in the process in the production of the desired ester product.

The extraction process of the invention is conducted at a temperature of about 35° C. to about 65° C. employing the same alcohol utilized in producing the desired diester. This is because it has been found that it is the most effective agent for the extraction of the acidified aqueous phase containing monester and other organic acid esters and other organic impurities which are present. For instance, where 2-ethylhexanol is utilized as the alcohol and phthalic anhydride is used as the precursor of phthalic acid, there is present in the acidified aqueous phase phthalic acid, the monester of phthalic acid, namely, octyl acid phthalate, and where sulfuric acid is used as a catalyst there is present octyl acid sulfate. The alcohol extraction agent is, on the other hand, relatively ineffective with respect to the extraction of inorganic impurities such as sulfuric acid.

As indicated by the following partition coefficients for the impurities which can be present in said first aqueous phase, said coefficient being obtained by dividing the concentration of the impurities present in the organic phase by the concentration of the impurities present in the aqueous phase, where the free acidity of the acidified water is from 0.03 to 0.1 Normal.

P: (dioctyl phthalate)—45
P: (octyl acid phthalate)—20
P: (sulfuric acid)—~0
P: (phthalic acid)—2.8

It is thus found that extraction of the first aqueous phase with 2-ethylhexanol simultaneously with or subsequent to acidification so as to provide a free acidity of about 0.03 to 0.1 Normal results in extraction of the main impurity in the waste water, namely the monester, and that the diester is extracted even more efficiently.

The mode of operation of the present invention has been described with respect to FIGS. 1, 2 and 3, specific features of the process relating to filtration and activated carbon treatment of the aqueous waste phases produced in the process and specific description of the waste water carbon treatment shown in FIG. 2 or an alternative evaporation stage disclosed in the process of FIG. 3 will now be described by way of example. Where not otherwise specified throughout this specification and claims, temperatures are given in degrees centigrade and parts, percentages, and proportions are by weight.

EXAMPLE 1

This example illustrates the treatment of waste water obtained from the reaction of phthalic anhydride and 2-ethylhexanol in the presence of tetra-n-butyl titanate as catalyst wherein the process is generally conducted in accordance with procedures of the prior art wherein the esterification reaction mixture is mixed with an aqueous alkali to solubilize the monester by-product therein and the mixture is allowed to separate into two phases, the first aqueous phase and the first organic phase. Said first aqueous phase is the process waste water which is subsequently treated in this example. Generally, the waste water can contain variable concentrations of the following impurities: octanol(2-ethylhexanol), dioctyl phthalate, disodium phthalate, mixed sodium and octyl phthalate, mixed sodium and octyl sulfate, sodium sulfate, and sodium hydroxide. The sulfates are derived from the sulfuric acid used in the acidification stage of the process and the sodium hydroxide is that used in the neutralization stage. Generally, the most abundant impurity is the mixed sodium and octyl sulfate which is responsible for the greatest part of the biological oxygen demand of the waste water. By operating in accordance with the process of the invention, it has been found that the color of the waste water can be improved by treatment with activated carbon and the sodium ion concentration can be reduced utilizing a washing step with water thus permitting recycling the organic phase subsequently separated from the waste water to the reaction process and utilizing the wastewater in the process generally.

To 100 grams of waste water obtained from the production of dioctyl phthalate, there were added 0.5 grams of activated carbon sold under the trademark "DARCO KB" and 1 gram of filter aid. The mixture was stirred at a temperature of 50° C. for two hours and then filtered using a Buchner funnel prepared with a ¼ inch precoat of filter aid using a water solution of the filter aid. The color of the waste water prior to activated carbon treatment and filtration was greater than 70 APHA and dark yellow. The color of the filtrate after carbon treatement of the waste water was 30 to 40 APHA and water white.

EXAMPLE 2

This example illustrates the combination of activated carbon treatment and water washing to upgrade the color obtained in DOP manufacture thus permitting the use of the organic layer separated therefrom in the process as well as the use of the water itself.

Five gallons of waste water from the production of dioctyl phthalate were treated in accordance with the procedure and proportions of Example 1. Thereafter, 2.5 gallons of the filtrate obtained were treated with 0.895 gallons of 6 percent sulfuric acid and 0.25 gallons of 2-ethylhexanol. The two phases which resulted were separated and the top organic phase was washed with 2 liters of distilled water, the two phases which were obtained were separated and the top organic layer was washed with 2 liters of distilled water and the layers separated. The organic phase obtained in the last separation was vacuum distilled and the organic phase remaining after distillation had an acid number of 137. Further analysis indicated 2.7 parts per million of $SO_4^{-2}$ ion and a sodium ion concentration of 28.4 parts per million. Monooctylphthalate concentration was 60.63 percent, dioctylphthalate concentration was 14.7 percent and 2-ethylhexanol concentration by difference was 24.7 percent, all by weight. Since this sample was treated both with activated carbon and by water washing, the color of the sample was similar to that disclosed in Example 1.

EXAMPLE 3

Dioctyl phthalate was prepared utilizing as a portion of the reactants the purified organic phase obtained in Example 2. There were charged to a one liter flask 170.69 grams of phthalic anhydride, 329.52 grams of 2-ethylhexanol, 10.13 grams of the organic purified product prepared in Example 2, and 0.21 grams of tetra-n-butyl titanate. The flask was purged with nitrogen and heated to a temperature of 168° C. and increased to a maximum temperature of 228° C., the reaction taking place over a period of 6 hours and 25 minutes. The product obtained was neutralized with sodium hydroxide to separate the diester from the unreacted phthalic acid or anhydride and the 2-ethylhexanol which remains unreacted. The organic phase obtained thereafter is separated and washed with water, steam stripped and filtered to purify the diester product. The dioctyl phthalate obtained had a color of 10 to 20 APHA, a water content of 0.026 percent by weight, a monooctylphthalate content of 0.033 percent by weight, and a 2-ethylhexanol content of 3.80 percent by weight. The acid number of the product was 0.56.

EXAMPLE 4

(Control—forming no part of this invention)

For comparison purposes, dioctyl phthalate was prepared in accordance with the procedure of Example 3 except that no purified recycle organic phase was added as a reactant. There were used 170.54 grams of phthalic anhydride, 329.73 grams of 2-ethylhexanol and 0.21 grams of tetra n-butyl titanate. The purified dioctyl phthalate which was obtained had the following analysis: color, 10–20 APHA; water, 0.035 percent by weight; monooctyl phthalate, 0.033 percent by weight; 2-ethylhexanol, less than 0.05 percent by weight; and an acid number of 0.112.

While this invention has been described with reference to certain specific embodiments, it will be recognized by those skilled in the art that many variations are possible without departing from the scope and spirit of the invention and it will be understood that it is intended to cover all changes and modifications of the invention disclosed herein for the purposes of illustration which do not constitute departures from the spirit and scope of the invention.

The embodiments of the invention in which an exclusive property or privilege is claimed are defined as follows:

1. In a continuous process for the esterification of phthalic acid or anhydride with at least one saturated aliphatic alcohol containing about 4 to about 10 carbon atoms, esterification being carried out with recycling of said alcohol used in a stoichiometric excess in the presence or absence of esterification catalysts wherein said esterification results from continuously feeding said phthalic acid or anhydride, said saturated alcohol, and an organic by-product of said process derived from the extraction of the waste water product of said process with an alcohol wherein said alcohol used for the extraction is the same as that used to form said phthalic ester and said esterification is conducted in a reactor stage by reacting said acid or anhydride with said aliphatic alcohol until a level of acid to ester conversion of at least 90 percent is reached, and wherein the water of esterification is removing from the reaction and condensed in a heat exchanger together with a portion of the alcohol used to esterify and the alcohol returned to the process for use in extraction of waste water produced in the process, and wherein neutralization is effected in a neutralizing stage of the resulting diester product also containing, as organic impurities, monoester, unreacted phthalic acid and said aliphatic alcohol, and other impurities with an aqueous alkali solution at a temperature of about 80° C. to 100° C., and thereafter forming a first organic phase and a first waste aqueous phase, and wherein said organic phase is separated by decanting and thereafter purified by steam stripping and carbon treatment to produce the desired diester product, the improvement wherein process waste water and said organic by-product of said process is purified and said by-product is recycled to said reactor stage without imparting color to said diester product by the following steps wherein
(a) said first waste aqueous phase is filtered to remove solids and passed through activated carbon to remove color bodies, and thereafter
(b) said first waste aqueous phase is mixed with an amount of said aliphatic alcohol to extract said organic impurities from the acidified first waste aqueous phase water while maintaining a temperature of about 35° C. to about 65° C., and
(c) a second organic phase is separated from a second waste aqueous phase by decantation,
(d) said second organic phase is washed and
(e) a third waste aqueous phase is separated from a third organic phase, and
(f) said third organic phase is recycled to said reactor stage.

2. The process of claim 1 wherein said esterification is conducted in the presence of an acidic catalyst.

3. The process of claim 2 wherein said catalyst is selected from the group consisting of sulfuric acid, benzene sulfonic acid, para toluene sulfonic acid, and mixtures thereof.

4. The process of claim 1 wherein said esterification is conducted in the presence of an amphoteric compound and wherein said compound is selected from the group consisting of divalent tin oxide, divalent tin oxylate, tin metal, bismuth oxide and mixtures thereof.

5. The process of claim 1 wherein said esterification is conducted in the presence of a lower alkyl titanium or zirconium ester catalyst.

6. The process of claim 5 wherein said alkyl ester catalyst contains about 3 to about 8 carbon atoms in the alkyl group.

7. The process of claim 6 wherein said alkyl ester catalyst is selected from the group consisting of isopropyl titanate, 2-ethylhexyl titanate, n-butyl titanate, and mixtures thereof.

8. The process of claim 7 wherein said alkyl ester catalyst is employed in the amounts of about 0.1 to about 3 percent by weight of the reactants and the esterification is carried out at a temperature of about 100° C. to 200° C. within said esterification reactor.

9. The process of claim 5 wherein the free acidity of the acidified waste water is greater than 0.03 Normal, said anhydride is phthalic anhydride, said alcohol is selected from the group consisting of 2-ethylhexanol-1, n-octanol-1, n-octanol-2, n-nonyl alcohol, decanol, and isodecanol, and said catalyst is n-butyl titanate.

10. The process of claim 9 wherein said alcohol is 2-ethylhexanol-1 which is used in excess of the stoichiometric amount with respect to said phthalic anhydride said amount being about 10 percent by weight excess of about 50 percent by weight excess based upon the weight of said anhydride.

11. The process of claim 10 wherein said 2-ethylhexanol-1 is used in the proportion of about 5 percent by weight to about 25 percent by weight based upon the weight of said first waste aqueous phase to extract said phase.

12. In a continuous process for the production of a diester of phthalic acid or anhydride by esterification thereof in at least one esterification reactor with at least one saturated aliphatic alcohol having about 4 to about 10 carbon atoms by an autocatalytic or catalytic esterification reaction utilizing said alcohol in a stoichiometric excess while continuously removing from the reaction and condensing the water of esterification together with a portion of said alcohol, recycling said water of esterification and said alcohol to the reaction which is conducted at an esterification temperature of about 150° C. to about 250° C. to obtain a conversion of said acid or anhydride of at least 90 percent whereupon the reaction mixture is mixed with an aqueous alkali to solubilize therein the monoester by-product and other organic impurities, the mixture is allowed to separate into two phases, a first aqueous waste phase and a first organic phase and thereafter said organic phase is washed with water and subsequently decolorized by steam distillation and filtration to yield the desired diester product, the improvement which comprises:
(a) treating said first aqueous waste phase by filtration with charcoal to remove solids and color bodies,
(b) acidifying said first aqueous phase with a strong acid to attain a free acidity of said phase which is greater than 0.03 Normal and mixing therewith about 5 to about 25 percent by weight of the same saturated aliphatic alcohol used in said esterification, said weight based upon the weight of said aqueous phase,
(c) separating the resulting mixture into a second organic phase and a second aqueous waste phase,
(d) mixing said second organic phase with about 50 to 200 percent by weight of water based upon the weight of said second organic phase, and
(e) separating the resulting mixture into a third organic phase and a third aqueous waste phase and recycling said third organic phase to said esterification reactor.

13. The process of claim 12 wherein said process is a catalytic esterification process conducted in the presence of an acid catalyst and said catalyst is n-butyl titanate, said anhydride is phthalic anhydride, and said alcohol is selected from the group consisting of butanol, n-octanol-1, n-octanol-2, 2-ethylhexanol-1, n-nonyl alcohol, decanol, and isodecanol.

14. The process of claim 13 wherein said alcohol is 2-ethylhexanol-1 and wherein said alcohol is used in excess of the stoichiometric amount based upon the phthalic anhydride weight of about 10 percent excess to about 50 percent excess by weight.

15. The process of claim 14 wherein all waste water streams in said process are either recycled to the process, or filtered through activated charcoal prior to discharge.

16. The process of claim 15 wherein all aqueous wastes in said process are recycled to the process, excess water being purged as required, and wherein the inorganic salts contained in said aqueous wastes are removed following evaporation of said aqueous wastes.

* * * * *